United States Patent [19]

Sprecker et al.

[11] Patent Number: 4,493,790

[45] Date of Patent: * Jan. 15, 1985

[54] ORGANOLEPTIC USE OF ISOPROPYL TETRAMETHYLINDANES

[75] Inventors: Mark A. Sprecker, Sea Bright; Robert P. Belko, Woodbridge; Roger E. Greene, Oakhurst, all of N.J.

[73] Assignee: International Flavors & Fragrances Inc., New York, N.Y.

[*] Notice: The portion of the term of this patent subsequent to Aug. 21, 2001 has been disclaimed.

[21] Appl. No.: 541,263

[22] Filed: Oct. 12, 1983

Related U.S. Application Data

[62] Division of Ser. No. 431,999, Sep. 30, 1982, Pat. No. 4,466,908.

[51] Int. Cl.$^3$ .............................................. C11B 9/00
[52] U.S. Cl. ................................. 252/522 R; 252/8.6; 252/174.11; 252/522 A; 424/69
[58] Field of Search ........................ 252/522 R, 522 A

[56] References Cited

U.S. PATENT DOCUMENTS 3,509,215 7/1970 Wood et al. ................... 252/522 R
4,352,748 10/1982 Traas et al. ..................... 252/522 R Primary Examiner—Anton H. Sutto
Attorney, Agent, or Firm—Arthur L. Liberman

[57] ABSTRACT

Described are isopropyl tetramethylindan musks defined according to the generic structure:

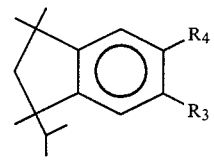

wherein
$R_3$ and $R_4$ are each acetyl or methyl with the provisos:
(a) one of $R_3$ or $R_4$ is methyl;
(b) when $R_4$ is methyl, then $R_3$ is acetyl and
(c) when $R_4$ is acetyl, $R_3$ is methyl and organoleptic uses thereof in augmenting or enhancing the aroma of perfume compositions, colognes and perfumed articles.

2 Claims, 8 Drawing Figures

FIG.6

GLC PROFILE FOR EXAMPLE II.

FIG.1

GLC PROFILE FOR EXAMPLE I.

FIG.2

NMR SPECTRUM FOR PEAK 10 OF FIG.1, EXAMPLE I.

FIG.3

IR SPECTRUM FOR PEAK 10 OF FIG.1, EXAMPLE I.

FIG.4

NMR SPECTRUM FOR PEAK II OF FIG.1, EXAMPLE I.

FIG.5

IR SPECTRUM FOR PEAK II OF FIG.1, EXAMPLE I.

FIG.7

NMR SPECTRUM FOR PEAK 61 OF FIG.6, EXAMPLE II.

FIG.8

IR SPECTRUM FOR PEAK 61 OF FIG.6, EXAMPLE II.

ORGANOLEPTIC USE OF ISOPROPYL TETRAMETHYLINDANES

This is a divisional of application Ser. No. 431,999, filed 9/30/82, now U.S. Pat. No. 4,466,908.

BACKGROUND OF THE INVENTION

Our invention relates to the preparation of novel acetyl isopropyl tetramethylindan musks, organoleptic uses thereof in augmenting or enhancing the aroma of perfume compositions, colognes and perfumed articles, as well as a process for preparing same and novel intermediate therefor.

There has been considerable work performed relating to substances which can be used to impart (or alter, modify or enhance) fragrance to (or in) various consumable materials. These substances are used to diminish the use of natural materials, some of which may be in short supply and to provide more uniform properties in the finished product. Sweet, ambrette seed-like and musky aroma characteristics are particularly desirable for many uses in several types of perfume compositions, colognes and perfumed articles (e.g. solid or liquid anionic, cationic, nonionic or zwitterionic detergents, fabric softener compositions, fabric softener articles, perfumed polymers, cosmetic powders and hair preparations).

The production of isochromans, for example, has been shown in the prior art and certain novel isochromans have recently been disclosed as outstanding musk fragrances. Such isochromans especially adpated for perfumery by virtue of their properties have been disclosed in Heeringa and Beets U.S. Pat. No. 3,360,530 issued on Dec. 26, 1967.

Acetyl tetralin musks such as that having the structure:

produced according to the reaction:

are disclosed in U.S. Pat. Nos. 2,752,404, 2,759,022 and 2,851,501 (commonly termed "Tonalide", for example).

Acetyl indan musk compounds, for example, having the structure:

is disclosed in Dutch published application No. 78 02038 corresponding to U.S. Pat. No. 4,352,748 issued on Oct. 5, 1982 and commonly termed "Traeseolide".

The Givaudan Corporation of Clifton, N.J. published in a series of 9 articles in the "Givaudanian" starting with January, 1968, a review article on the "Chemistry of the Aromatic Musks" and in said review article discloses the following compounds with their properties:

TABLE I

| Structure of Compound | Odor Evaluation |
|---|---|
| | Musky and woody |
| | Weak musk odor |
| | Odorless |
| | Odorless |

The Givaudanian articles thus disclose compounds defined according to the generic structure:

wherein R is methyl, ethyl, n-propyl and isobutyl but do not disclose compounds defined according to the structures:

(wherein R is isopropyl).

Nothing in the prior art discloses the rearrangement reactions:

and enabling efficient production of the compounds having the structures:

The compounds having the structures:

have unexpected, unobvious and advantageous organoleptic properties in perfumery with respect to the other compounds
having the structure:

wherein R represents methyl, ethyl, n-propyl and isobutyl.

BRIEF DESCRIPTION OF THE DRAWINGS

and wherein one of $R_1$ or $R_2$ is methyl and the other of $R_1$ or $R_2$ is hydrogen.

(conditions: $CFCl_3$ Solvent; 100 MHz Field Strength), wherein one of $R_1$ or $R_2$ is methyl and the other of $R_1$ or $R_2$ is hydrogen.

wherein one of $R_1$ or $R_2$ is methyl and the other of $R_1$ or $R_2$ is hydrogen.

(Conditions: $CFCl_3$ Solvent; 100 MHz Field Strength) wherein one of $R_1$ or $R_2$ is hydrogen and the other of $R_1$ or $R_2$ is methyl.

wherein one of $R_1$ or $R_2$ is hydrogen and the other of $R_1$ or $R_2$ is methyl.

(conditions: CFCl$_3$ Solvent; 100 MHz Field Strength).

DETAILED DESCRIPTION OF THE DRAWINGS

Figure 1:
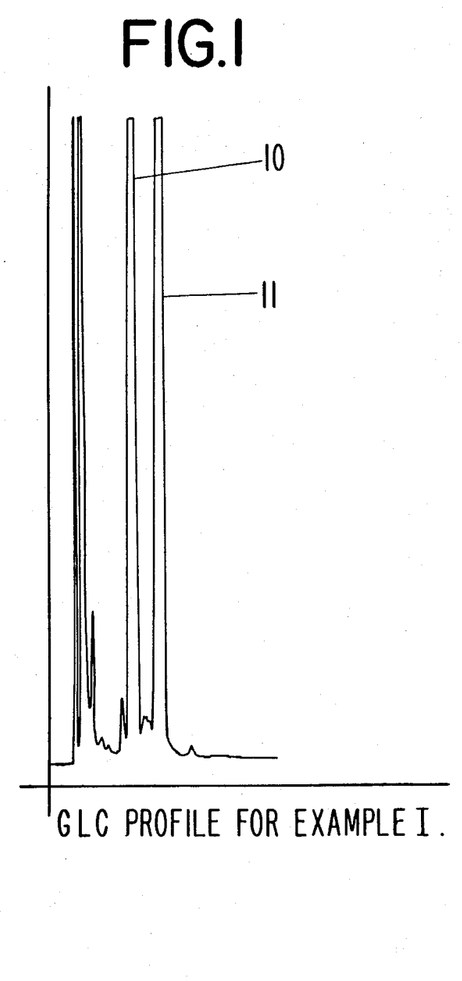
FIG. 1 is the GLC profile for the reaction product of Example I containing the compounds defined according to the structures.

FIG. 1 is the GLC profile for the reaction product of Example I (conditions: 220° C. isothermal; SE-30 column). The peak indicated by reference numeral "10" is the peak for the compounds having the structures:

-continued
and

The peak indicated by reference numeral "11" is for the compound having the structure:

wherein one of $R_1$ or $R_2$ is hydrogen and the other of $R_1$ or $R_2$ is methyl.

Figure 6:
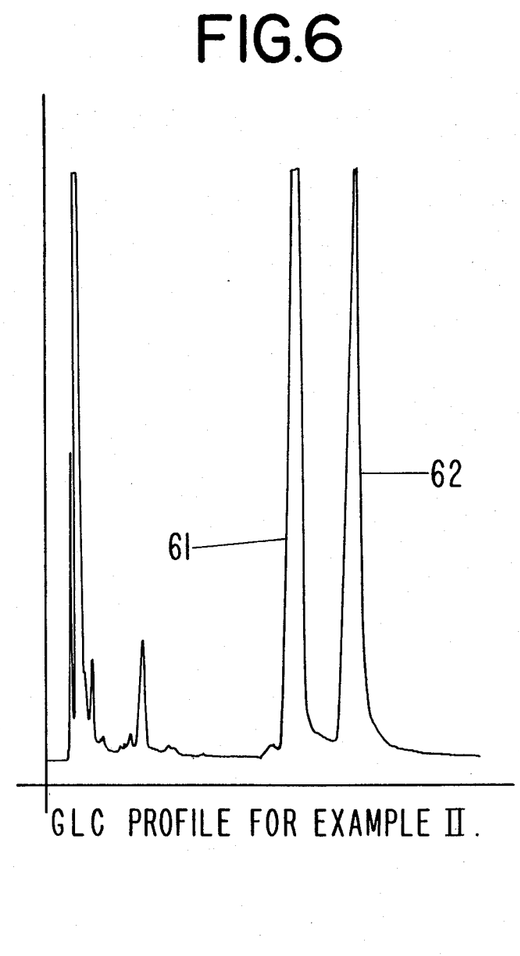
FIG. 6 is the GLC profile for the reaction product of Example II containing the compounds having the structures.

FIG. 6 is the GLC profile for the reaction product of Example II. The peak indicated by reference numeral "61" is the peak for the compounds having the structures:

The peak indicated by reference numeral "62" is the peak for the compound having the structure:

(Conditions: 220° C. isothermal SE-30 column).

THE INVENTION

It has now been discovered that novel solid and liquid perfume compositions, colognes and perfumed articles having sweet, ambrette seed-like and musky aroma characteristics may be provided by the acetyl indan derivatives defined according to the structures:

and mixtures of these acetyl indanes with the acetyl tetralin derivative having the structure:

which mixtures are produced according to the process of first rearranging hexamethyl tetralin with an aluminum chloride catalyst according to the reactions:

and and then acetylating the resulting tetramethyl isopropyl indan with the compound defined according to the structure:

wherein Z represents acetoxy, chloro or bromo, in order to form the acetyl indanes defined according to the structures:

according to the reactions:

wherein one of $R_1$ or $R_2$ is methyl and the other of $R_1$ or $R_2$ is hydrogen and one of $R_3$ or $R_4$ is acetyl and the other of $R_3$ or $R_4$ is methyl.

The acetyl hexamethyl tetralin "Tonalide" is well represented in the literature and has the structure:

This material is indicated to be produced according to the reaction:

If this reaction is carried out in tetrachloroethylene so that all of the aluminum trichloride is dissolved, the compound having the structure:

is formed.

However, in the presence of solid aluminum chloride where the aluminum chloride is not all dissolved, a rearrangement takes place in tetrachloroethylene according to the reactions:

and

On the other hand, if one attempts to rearrange "Tonalide" having the structure:

using the same conditions whereby it is attempted to carry out the reaction:

this reaction will not take place. Accordingly, our invention requires the use of the hydrocarbon having the structure:

as a starting material wherein one of $R_1$ or $R_2$ is hydrogen and the other of $R_1$ or $R_2$ is methyl.

The reaction of our invention can be illustrated thusly:

although the acetyl chloride may be replaced by acetic anhydride. The compounds thus formed can be separated by ordinary separation techniques such as fractional distillation and/or commercial chromatographic separations.

In carrying out the reactions:

and the reactions are preferably carried out in the presence of a tetrachloroethylene solvent which is saturated with aluminum trichloride and in the presence of an excess of aluminum chloride. The weight ratio of aluminum chloride:tetrachloroethylene may vary from about 35:100 up to about 60:100 but weight ratios of aluminum trichloride above 60:100 may also be used without any adverse effects upon the reactant.

The temperature of reaction may vary from about $-10°$ C. up to $+10°$ C. with a preferred temperature of reaction of about 0° C. when carrying out the reaction for a period of about 1 hour. The time of reaction may vary from about 0.5 hours up to about 10 hours for higher yields but the optimum time of reaction at 0° C. is about 1 hour when using a ratio of aluminum chloride:tetrachloroethylene of about 35:100.

The weight ratio of tetrachloroethylene:hydrocarbon defined according to the structure:

wherein one of $R_1$ or $R_2$ is hydrogen and the other of $R_1$ or $R_2$ is methyl may vary from about 100:75 down to about 100:25 with a preferred weight ratio of tetrachloroethylene:compound having the structure:

of about 100:50.

The resulting reaction product may then be acylated with acetyl chloride, acetyl bromide or acetic anhydride and standard acylation procedures may be used. Thus, the temperature of reaction may vary from about $-10°$ C. up to $+20°$ C. The mole ratio of acyl halide or acetic anhydride:compound defined according to the structure:

wherein one of $R_1$ or $R_2$ is hydrogen and the other of $R_1$ or $R_2$ is methyl, may vary from about 0.5:1 up to about 1:0.5 with a preferred mole ratio of 1:1.

At the end of the reaction, the resulting reaction mixture containing the compounds defined according to the structures:

may be fractionally distilled or otherwise separated by commercial chromatographic separation means.

In the alternative, the preparation of the compounds defined according to the structures:

may be carried out according to the reaction:

(wherein Z represents acetoxy, chloro or bromo). The mole ratio of compound having the structure:

wherein one of $R_1$ or $R_2$ is hydrogen and the other of $R_1$ or $R_2$ is methyl, may vary from 0.5:1 up to about 1:0.5 with a preferred mole ratio of 1:1.

The reaction is carried out using tetrachloroethylene saturated with aluminum chloride and an excess of aluminum trichloride. Thus, the weight ratio of aluminum trichloride:tetrachloroethylene may vary from about 1:4 up to about 1:1 with a weight ratio of about 1:3 being preferred.

The weight ratio of aluminum chloride:hydrocarbon defined according to the structure:

may vary from about 0.5:1 up to about 1:0.5 with a preferred mole ratio of about 1:1.3 of aluminum chloride:hydrocarbon defined according to the structure:

being preferred.

The reaction temperature may vary from about −10° C. up to about +10° C. with a preferred reaction temperature range of from about 0° C. up to about 5° C. The reaction time may vary from about 3 hours up to about 10 hours with a preferred time of reaction (including time for addition of the acetyl chloride) being about 5 hours at a reaction temperature of between 0° and 5° C.

The acetyl isopropyl tetramethylindan musks and one or more auxiliary perfume ingredients including, for example, alcohols, aldehydes, nitriles, esters, cyclic esters, ketones other than the acetyl isopropyl tetramethylindan musks of our invention, ethers, natural essential oils and synthetic essential oils may be admixed so that the combined odors of the individual components produce a pleasant and desired fragrance particularly and preferably in musky and "animal-like" fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation and (d) topnotes which are usually low-boiling, fresh-smelling materials.

In perfume compositions, it is the individual components which contribute to its particular olfactory characteristics, but the overall effect of the perfume composition will be the sum of the effects of each of the ingredients. Thus, the acetyl isopropyl tetramethylindan musks can be used to alter the aroma characteristics in a perfume composition, for example, by utilizing or moderating the olfactory reaction contributed by at least one other ingredient in the composition.

The amount of acetyl isopropyl tetramethylindan musks of our invention which will be effective in perfume compositions depends upon many factors including the other ingredients, their amounts and the effects which are desired. It has been found that perfume compositions containing as little as 0.01% of the acetyl isopropyl tetramethylindan musks and even less (e.g. 0.005%) can be used to impart a sweet, ambrette seed-like, musky aroma to soaps, anionic, cationic, nonionic and zwitterionic detergents, fabric softening compositions, fabric softener articles, cosmetic powders, hair preparations, and perfumed polymers, e.g. perfume-containing microporous polypropylene and perfume-containing microporous polyethylene and perfume-containing microporous polyurethane-polycaprolactone copolymers. The amount employed can range up to 50% of the fragrance components and can range up to 0.5% by weight of the perfumed article and will depend upon considerations of cost, nature of the end product, the effect desired on the finished product and the particular fragrance sought.

The acetyl isopropyl tetramethylindan musks are useful taken alone or in perfume compositions as olfactory components in anionic, cationic, nonionic and zwitterionic detergents, soaps, fabric softener compositions, fabric softener articles for use in clothes driers, (e.g. BOUNCE ®, a registered trademark of the Proctor & Gamble Company of Cincinnati, Ohio), space odorants and deodorants, perfumes, colognes, toilet water, bath preparations such as lacquers, brilliantines, creams and pomades; deodorants, hand lotions and sun screens; powders such as talcs, dusting powders, face powders and the like.

When used as an olfactory component in perfume compositions or perfumed articles, such as anionic, cationic, nonionic and zwitterionic detergents and in fabric softener compositions and fabric softener articles (e.g. for use in clothing driers) as little as 0.05% of the acetyl isopropyl tetramethylindan musks of our invention will suffice to impart an intense sweet, ambrette seed, musky fragrance. Generally no more than 5% of the acetyl isopropyl tetramethylindan musks based on the ultimate end product is required in the perfume composition or the perfumed article.

The range of acetyl isopropyl tetramethylindan musks useful in augmenting or enhancing the aroma of a perfumed article such as a solid or liquid anionic, cationic, nonionic or zwitterionic detergent is from about 0.05% by weight of the perfumed article up to about 5.0% by weight of the perfumed article.

In addition, the perfume composition or fragrance composition of our invention can contain a vehicle or carrier for the acetyl isopropyl tetramethylindan musks. The vehicle can be a liquid such as a non-toxic alcohol, a non-toxic glycol or the like. An example of a non-toxic alcohol is ethyl alcohol. An example of a non-toxic glycol is 1,2-propylene glycol. The carrier can be an absorbent solid such as a gum, (e.g. gum arabic, xanthan gum or guar gum) or components for encapsulating the composition (such as gelatin) by means of coacervation or such as a urea formaldehyde polymer whereby a polymeric shell is formed around a liquid perfume oil center.

The following examples are illustrative and the invention is to be considered as restricted thereto only as indicated in the appended claims. All parts and percentages given herein are by weight unless otherwise specified.

EXAMPLE I and

Into a 250 ml reaction flask equipped with stirrer, thermometer, reflux condenser, dropping funnel and cooling bath is placed 50 grams of a mixture of compounds defined according to the structure:

wherein one of $R_1$ or $R_2$ is methyl and the other of $R_1$ or $R_2$ is hydrogen, and 100 grams of tetrachloroethylene. The resulting mixture is cooled to 0° C. and 35 grams of aluminum trichloride is added. The reaction mixture is then stirred at 0° C. for a period of 1 hour. At the end of this one hour period, the mixture contains the following compounds:

and wherein one of $R_1$ or $R_2$ is hydrogen and the other of $R_1$ or $R_2$ is methyl.

FIG. 1 is the GLC profile for the reaction product of Example I. (Conditions: 220° C. isothermal; SE-30 column). The peak indicated by reference numeral "10" is the peak for the compounds defined according to the structure:

wherein one of $R_1$ or $R_2$ is hydrogen and the other of $R_1$ or $R_2$ is methyl. The peak indicated by reference numeral "11" is the peak for the compounds defined according to the structure:

wherein one of $R_1$ or $R_2$ is hydrogen and the other of $R_1$ or $R_2$ is methyl.

Figure 2:
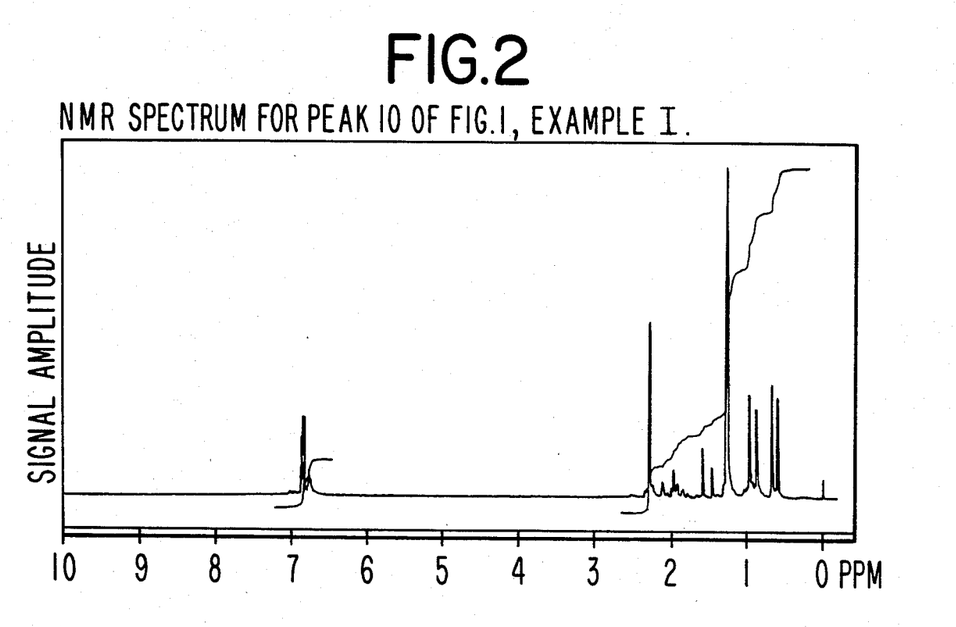
FIG. 2 is the NMR spectrum for the peak indicated by reference numeral "10" on the GLC profile of FIG. 1 and is for the compounds having the structure.

FIG. 2 is the NMR spectrum for the peak indicated by reference numeral "10" on FIG. 1 for the compounds defined according to the structure:

wherein one of $R_1$ or $R_2$ is methyl and the other of $R_1$ or $R_2$ is hydrogen (conditions: Solvent: $CFCl_3$; Field Strength: 100 MHz).

The assignments for the hydrocarbon compounds for this NMR spectrum are given for the following structures:

and thusly:

$\delta$0.65, d, J=6 Hz; and 0.97, d, J=6 Hz, 6H, methyl groups "A"

$\delta$1.26 and $\delta$1.28-2 singlets, 9H, methyl groups "B"

$\delta$1.46, 1.60, 1.97 and 2.10; AB quartet, 2H, hydrogens "C" and "D"

$\delta$1.79 to 2.10, m, 1H, hydrogen "E"

$\delta$1.29, s, 3H, methyl group "F"

$\delta$6.70 to 6.86; m, 3H, aromatic protons "G".

Figure 3:
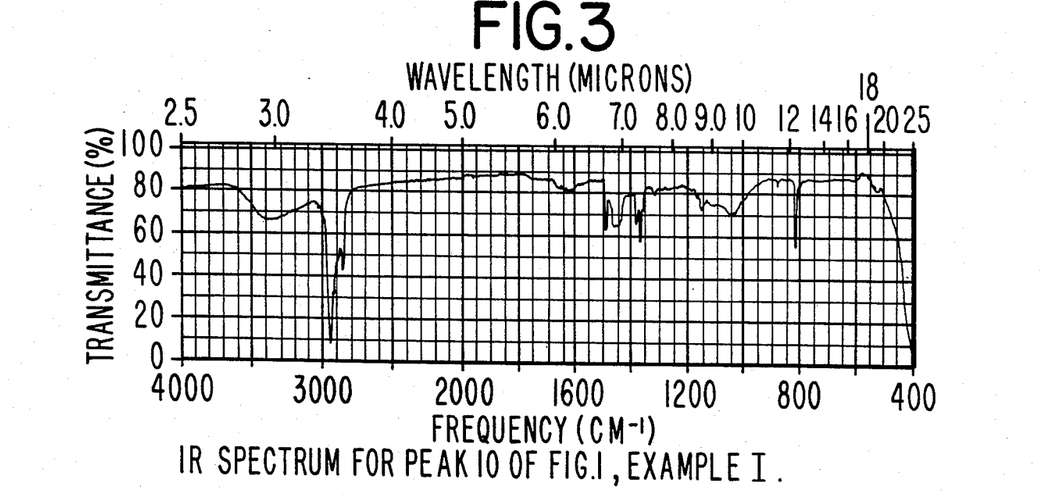
FIG. 3 is the infra-red spectrum for the peak indicated by reference numeral "10" on the GLC profile of FIG. 1 for the compounds having the structure.

FIG. 3 is the infra-red spectrum for the peak indicated by reference numeral "10" on the GLC profile of FIG. 1. This peak is for the compounds having the structure:

wherein one of $R_1$ or $R_2$ is hydrogen and the other of $R_1$ or $R_2$ is methyl.

The significant peaks in this IR spectrum in descending strength are as follows:

2958 cm$^{-1}$
2925
2862
812
1370

Figure 4:
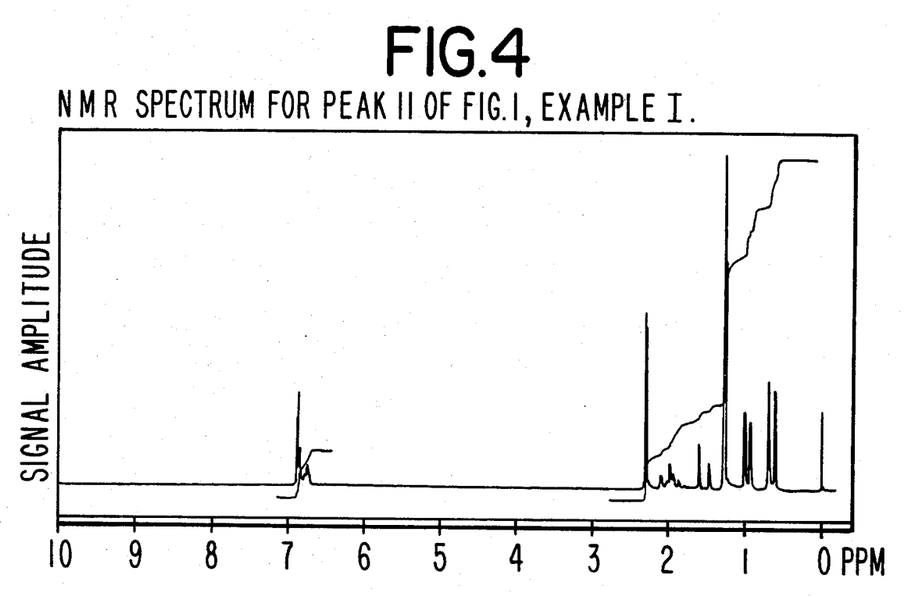
FIG. 4 is the NMR spectrum for the peak indicated by reference numeral "11" on FIG. 1 and is for the compound having the structure.

FIG. 4 is the NMR spectrum for the peak indicated by reference numeral "11" of the GLC profile of FIG. 1 for the compound defined according to the structure:

(conditions: $CFCl_3$ Solvent: 100 MHz Field Strength).

Figure 5:
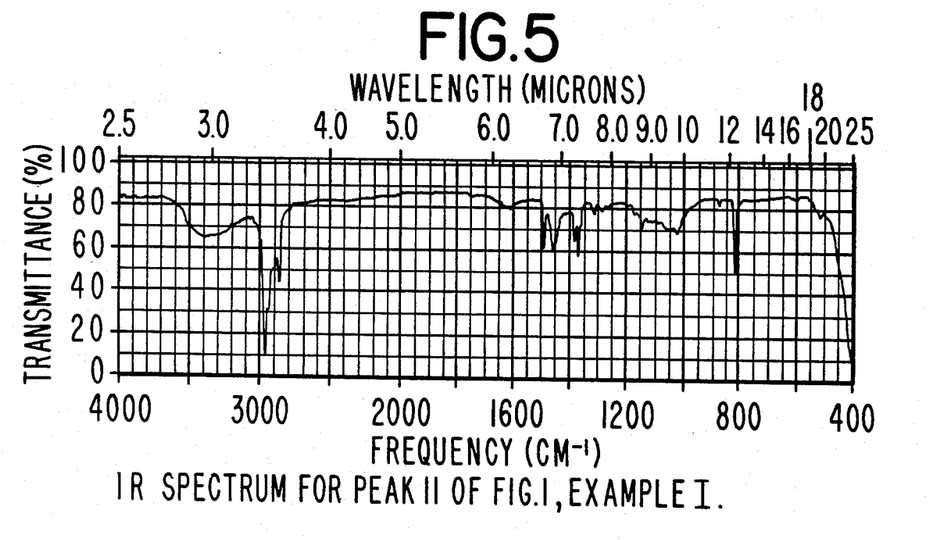
FIG. 5 is the infra-red spectrum for the peak indicated by reference numeral "11" on the GLC profile of FIG. 1 and is for the compound having the structure.

FIG. 5 is the infra-red spectrum for the peak indicated by reference numeral "11" of the GLC profile of FIG. 1 for the compound having the structure:

EXAMPLE II

PREPARATION OF ACETYL ISOPROPYL TETRAMETHYLINDAN

Reaction:

Into a 10 liter reaction vessel equipped with stirrer, thermometer and reflux condenser is placed 3,000 grams of tetrachloroethylene and 961 grams of anhydrous aluminum chloride. With stirring, the resulting liquid is cooled to 0° C.

1360 grams of the compound defined according to the structure:

(a mixture, wherein in the mixture one of $R_1$ and $R_2$ is methyl and the other of $R_1$ and $R_2$ is hydrogen) is then added to the resulting mixture maintaining the reaction temperature at 0°-5° C.

Over a period of 3 hours while maintaining the reaction mass at 0°-5° C., 542 grams of acetyl chloride is added to the reaction mass.

At the end of the 3 hour period, the reaction mass is stirred for an additional 2 hours at 0°-5° C.

The reaction mass is then distilled on a fractional distillation column yielding the following fractions:

| Fraction Number | Vapor Temp. (°C.) | Liquid Temp. (°C.) | Pressure mm/Hg. | Weight of Fraction (grams) |
| --- | --- | --- | --- | --- |
| 1 | 23/35 | 23/40 | 100/50 | 2000 |
| 2 | 27 | 60 | 10 | 2430 |
| 3 | 75 | 150 | 2 | 35.0 |

-continued

| Fraction Number | Vapor Temp. (°C.) | Liquid Temp. (°C.) | Pressure mm/Hg. | Weight of Fraction (grams) |
| --- | --- | --- | --- | --- |
| 4 | 125 | 155 | 2 | 114.5 |
| 5 | 123 | 155 | 2 | 25.1 |
| 6 | 123 | 156 | 2 | 19.4 |
| 7 | 123 | 156 | 2 | 93.2 |
| 8 | 123 | 157 | 2 | 103.2 |
| 9 | 125 | 158 | 2 | 116.0 |
| 10 | 128 | 159 | 2 | 112.5 |
| 11 | 133 | 160 | 2 | 115.2 |
| 12 | 134 | 160 | 2 | 116.5 |
| 13 | 134 | 160 | 2 | 99.3 |
| 14 | 134 | 163 | 2 | 92.0 |
| 15 | 134 | 172 | 2 | 115.3 |
| 16 | 129 | 205 | 2 | 79.7 |
| 17 | 125 | 250 | 2 | 21.7 |

Fractions 7-15 are bulked and re-distilled on an 8"×0.5" Goodloe column to yield the following fractions:

| Fraction Number | Vapor Temp. (°C.) | Liquid Temp. (°C.) | Pressure mm/Hg. | Reflux Ratio | Weight of Fraction (grams) | % Acetyl isopropyl tetramethylindan |
| --- | --- | --- | --- | --- | --- | --- |
| 1 | 23/100 | 23/148 | 1/1 | 9:1 | 6.9 | 85 |
| 2 | 100 | 148 | 0.9 | 9:1 | 4.8 | 92 |
| 3 | 165 | 148 | 0.8 | 9:1 | 6.6 | 93 |
| 4 | 110 | 150 | 0.6 | 9:1 | 12.2 | 95 |
| 5 | 105 | 156 | 0.6 | 9:1 | 16.2 | 96 |
| 6 | 112 | 157 | 0.5 | 9:1 | 19.8 | 96 |
| 7 | 106 | 156 | 0.3 | 9:1 | 20.0 | 96 |
| 8 | 108 | 156 | 0.3 | 9:1 | 24.9 | 97 |
| 9 | 111 | 156 | 0.3 | 9:1 | 25.9 | 92 |
| 10 | 111 | 156 | 0.3 | 9:1 | 27.2 | 91 |

FIG. 6 is the GLC profile for the reaction mass at the end of the period of addition of the acetyl chloride to the reaction mass. (Conditions: 220° C. isothermal; SE-30 column.)

Figure 7:
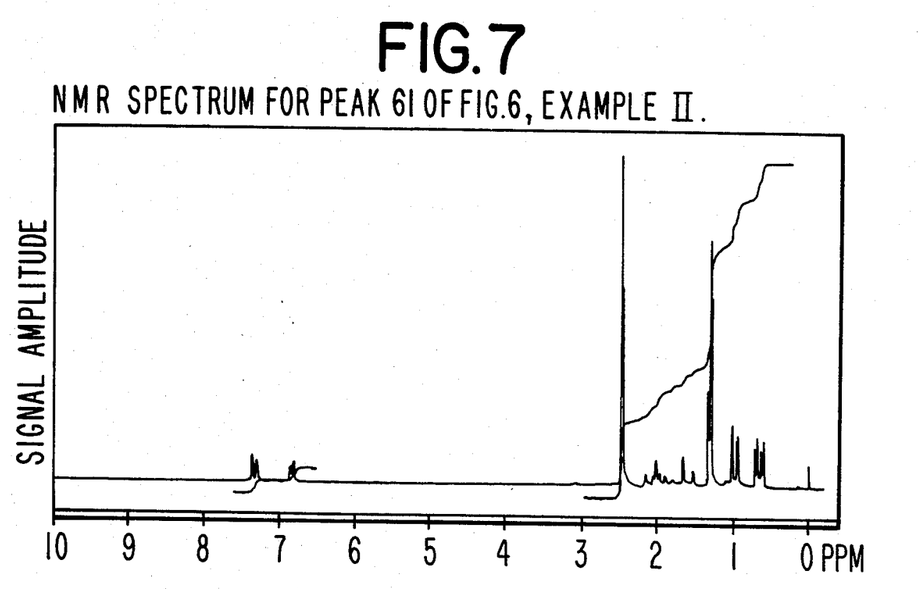
FIG. 7 is the NMR spectrum for the peak indicated by reference numeral "61" on FIG. 6 and is for the compounds having the structures.

The peak indicated by reference numeral "61" is the peak for the reaction product which is a mixture containing compounds having the structures:

The peak indicated by reference numeral "62" is the peak for the compounds defined according to the structures:

FIG. 7 is the NMR spectrum for the peak indicated by reference numeral "61" on the GLC profile of FIG. 6 (conditions: CFCl$_3$ Solvent; Field Strength: 100

MHz). Peak 61 of FIG. 6 contains the compounds defined according to the structures:

The peaks on the NMR spectrum define the structure:

with the following assignments:
δ0.65; d; J=6 Hz and δ0.67; d; J=6 Hz and δ0.97; d; J=6 Hz.6$\underline{H}$, methyl groups "A"
δ1.26, δ1.28, δ1.30-3 singlets, 9$\underline{H}$, methyl groups "B"
δ1.50, 1.64, 2.05 and 2.65; AB quartet, 2$\underline{H}$, hydrogens "C" and "D"
δ1.82 to 2.08, m, 1$\underline{H}$, hydrogen "E"
δ2.45 and 2.47, 2 singlets, 6$\underline{H}$, methyl groups "F"
δ6.81; 6.84; 7.30; and 7.37; singlets, 2$\underline{H}$, H"G"

Figure 8:
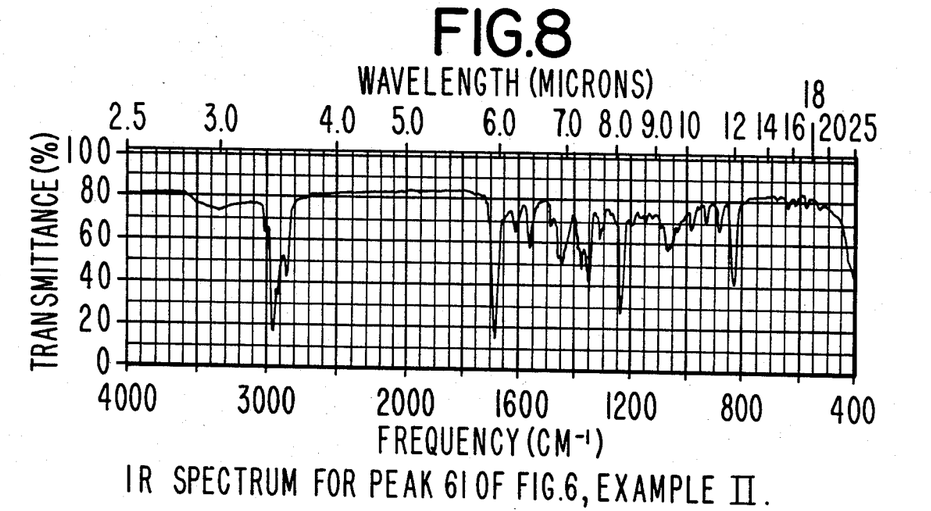
FIG. 8 is the infra-red spectrum for the peak indicated by reference numeral "61" on the GLC profile of FIG. 6 for the reaction product of Example II and is for the compounds having the structures.

FIG. 8 is the infra-red spectrum for the peak indicated by reference numeral "61" on the GLC profile of FIG. 6 for the compounds defined according to the structures:

The assignments for the infra-red peaks are, in descending order:
1680 cm$^{-1}$ (carbonyl)
2960
1230
2920
860
2860

EXAMPLE III

MUSK PERFUME FORMULATION

The following musk perfume formulation is prepared:

| Ingredients | Parts by Weight |
|---|---|
| Musk ambrette | 200 |
| Musk ketone | 200 |
| Beta ionone | 50 |
| Vetiveryl acetate | 50 |
| Sandalwood oil | 100 |
| Benzyl benzoate | 400 |
| Mixture of compounds defined according to the structures: [structures shown] prepared according to Example II, bulked distillation fractions 5–18 from final distillation | 20 |

The mixture of acetyl isopropyl tetramethylindans prepared according to Example II imparts to this musk formulation a natural sweet, ambrette seed aroma with great intensity.

EXAMPLE IV

PREPARATION OF A SOAP COMPOSITION

One hundred grams of soap chips are mixed with one gram of one of the materials set forth in Table II below until a substantially homogeneous composition is obtained. The resulting mixture is heated to a melt under 8 atmospheres pressure and a nitrogen atmosphere and molded into soap cakes which are then cooled and tested. The perfumed soap composition manifests an excellent aroma as set forth in Table II below:

TABLE II

| Perfume Ingredient | Aroma Evaluation |
|---|---|
| Mixture of compounds defined according to the structures: | A sweet, ambrette seed-like, musk aroma. |

TABLE II-continued

| Perfume Ingredient | Aroma Evaluation |
|---|---|
|  and  prepared according to Example II, bulked distillation fractions 5-8 from final distillation. | |
| Perfume composition of Example III | An intense, musk aroma with a natural sweet, ambrette seed undertone. |

EXAMPLE V

PREPARATION OF A COLOGNE AND HANDKERCHIEF PERFUME

The perfume substances of Table II of Example IV are incorporated into a cologne at concentrations of 1.5%, 2.0%, 2.5%, 3.0%, 3.5% and 4.0% in 80%, 85% and 90% aqueous ethanol; and into handkerchief perfumes at concentrations of 15%, 20%, 25% and 30% (in 85%, 90% and 95% aqueous ethanol). Distinct and definitive fragrances are produced and imparted to the colognes and handkerchief perfumes at each of the levels indicated in accordance with the aroma profiles set forth in Table II of Example IV supra.

EXAMPLE VI

PREPARATION OF COSMETIC POWDER COMPOSITIONS

Cosmetic powders are prepared by mixing in a ball mill one hundred grams of talcum powder with 0.15 grams of each of the substances in Table II of Example IV. The resulting powders have excellent aromas as set forth in Table II of Example IV.

EXAMPLE VII

DRIER-ADDED FABRIC SOFTENER ARTICLE

Utilizing the procedure of Example I of Column 15 of U.S. Pat. No. 3,632,396 (the specification of which is incorporated by reference herein), a non-woven cloth substrate useful as a drier-added fabric softening article of manufacture is prepared wherein the substrate, the substrate coating and the outer coating and the perfuming material are as follows:
1. a water "dissolvable" paper ("Dissolvo Paper");
2. Adogen 448 (m.p. about 140° F.) as the substrate coating and
3. an outer coating having the following formulation (m.p. about 150° F.):
57% $C_{20-22}$ HAPS
22% isopropyl alcohol
20% antistatic agent
1% of one of the perfumery substances of Table II of Example IV.

Fabric softening compositions prepared as set forth above having aroma characteristics as set forth in Table II of Example IV consist of a substrate having a weight of about 3 grams per 100 square inches, a substrate coating of about 1.85 grams per 100 square inches of substrate, an outer coating of about 1.4 grams per 100 square inches of substrate thereby providing a total aromatized substrate and outer coating weight ratio of about 1:1 by weight of the substrate. Aromas set forth in Table II of Example IV are imparted in a pleasant manner to the head space in the drier on operation thereof using said drier-added fabric softening non-woven fabric.

EXAMPLE VIII

PREPARATION OF A SOAP COMPOSITION

One hundred grams of soap chips are prepared according to Example V of U.S. Pat. No. 4,058,490 (the specification of which is incorporated by reference herein) issued on Nov. 15, 1977 as follows:

"The sodium salt of an equal mixture of $C_{10}/C_{14}$ alkane sulfonates (95% active), 40 lbs. is dissolved in a mixture of 80 lbs. of anhydrous isopropanol and 125 lbs. of deionized water at 150° F. In this mixture is dissolved 10 lbs. of partially hydrogenated coconut oil fatty acids and 15 lbs. of sodium mono-$C_{14}$-alkyl maleate, and the pH of this solution is adjusted to 6.0 by the addition of a small amount of a 50% aqueous solution of NaOH. The isopropanol is distilled off and the remaining aqueous solution is dried. The resulting solid actives are then blended in a chip mixer with 10 lbs. water, 0.2 lb. titanium hydroxide."

The resulting blend is then mixed on an individual basis, separately, with one gram of each of the substances of Table II of Example IV supra until a homogeneous composition is obtained. The perfumed soap compositions each manifest excellent aromas as set forth in Table II of Example IV supra.

What is claimed is:
1. A process for augmenting or enhancing the aroma of a consumable material selected from the group consisting of perfume compositions, colognes and perfumed articles comprising the step of adding to said perfume composition, cologne or perfumed article an aroma augmenting or enhancing quantity of a product consisting essentially of a mixture of compounds having the structures:

wherein a major proportion of the mixture consists of the compound having the structures:

and produced according to the process consisting of the steps of:
(i) first rearranging hexamethyl tetralin with an aluminum chloride catalyst according to the reactions:

and said first reaction taking place in the presence of tetrachloro ethylene solvent which is saturated with aluminum trichloride, said reaction taking place in the presence of an excessive aluminum chloride, the weight ratio of aluminum chloride:-tetrachloro ethylene varying from about 35:100 up to about 60:100, the temperature of said first reaction varying from about −10° C. up to +10° C. and the time of reaction varying from about 0.5 hours up to about 10 hours, the weight ratio of tetrachloro ethylene:hydrocarbon reactant having the structure:

wherein one of $R_1$ or $R_2$ is hydrogen and the other of $R_1$ or $R_2$ is methyl varying from about 100:75 down to about 100:25; and
(ii) acylating the resulting product with a compound having the structure:

wherein Z represents a moiety selected from the group consisting of acetoxy, chloro and bromo, the reaction being carried out at a temperature of from about −10° up to about +20° C.; the mole ratio of compound having the structure:

to the compound defined according to the structure:

wherein one of $R_1$ or $R_2$ is hydrogen and the other of $R_1$ or $R_2$ is methyl varying from about 0.5:1 up to 1:0.5; and then
(iii) subjecting the resulting reaction product to fractional distillation whereby a mixture of compounds having the structures:

is isolated with the major part of said mixture being compounds having the structures:

and

2. A process for augmenting or enhancing the aroma of a consumable material selected from the group consisting of perfume compositions, colognes and perfumed articles comprising the step of adding to said perfume composition, cologne or a perfumed article an aroma augmenting or enhancing quantity of a composition of matter consisting essentially of a mixture of compounds having the structures:

-continued with a major proportion of the mixture being compounds having the structures:

produced according to the process of the steps of:
(i) intimately admixing the compound having the structure:

with the compound having the structure:

wherein one of $R_1$ or $R_2$ is hydrogen and the other of $R_1$ or $R_2$ is methyl; and wherein Z is a moiety selected from the group consisting of acetoxy, chloro and bromo, the reaction being carried out in the presence of tetrachloro ethylene saturated with aluminum chloride and in the presence of an excess of aluminum chloride with the weight ratio of aluminum trichloride:tetrachloro ethylene varying from about 1:4 up to about 1:1; the weight ratio of aluminum chloride:hydrocarbon defined according to the structure:

varying from about 0.5:1 up to about 1:0.5; the reaction temperature varying from about −10° C. up to about +10° C.; the reaction time varying from about 3 hours up to about 10 hours; the mole ratio of compound having the structure:

to compound having the structure:

varying from about 0.5:1 up to about 1:0.5; and then
(ii) fractionally distilling the resulting product thereby recovering a mixture of compounds having the structures:

with a major proportion of the mixture being compounds having the structures:

* * * * *